(12) United States Patent
Ben-Barak et al.

(10) Patent No.: US 7,714,398 B2
(45) Date of Patent: May 11, 2010

(54) NANOELECTRONIC MEASUREMENT SYSTEM FOR PHYSIOLOGIC GASES AND IMPROVED NANOSENSOR FOR CARBON DIOXIDE

(75) Inventors: Nadav Ben-Barak, Berkeley, CA (US); Daniel M. Chang, Danville, CA (US); Jean-Christophe P. Gabriel, Pinole, CA (US); Vikram Joshi, Newington, CT (US); Joseph Niemann, Fremont, CA (US); Alexander Star, Pittsburgh, PA (US); Christian Valcke, Orinda, CA (US)

(73) Assignee: Nanomix, Inc., Emeryville, CA (US)

( * ) Notice: Subject to any disclaimer, the term of this patent is extended or adjusted under 35 U.S.C. 154(b) by 395 days.

(21) Appl. No.: 11/390,493

(22) Filed: Mar. 27, 2006

(65) Prior Publication Data

US 2010/0056892 A1 Mar. 4, 2010

Related U.S. Application Data

(63) Continuation-in-part of application No. 11/019,792, filed on Dec. 20, 2004, now Pat. No. 7,547,931, and a continuation-in-part of application No. 10/940,324, filed on Sep. 13, 2004, and a continuation-in-part of application No. 10/846,072, filed on May 14, 2004, and a continuation-in-part of application No. 10/773, 631, filed on Feb. 6, 2004, now abandoned, and a continuation-in-part of application No. 10/656,898, filed on Sep. 5, 2003, now abandoned.

(60) Provisional application No. 60/408,547, filed on Sep. 5, 2002, provisional application No. 60/445,654, filed on Feb. 6, 2003, provisional application No. 60/471, 243, filed on May 16, 2003, provisional application No. 60/502,485, filed on Sep. 12, 2003, provisional application No. 60/531,079, filed on Dec. 18, 2003, provisional application No. 60/665,153, filed on Mar. 25, 2005, provisional application No. 60/668,879, filed on Apr. 5, 2005, provisional application No. 60/748,834, filed on Dec. 9, 2005.

(51) Int. Cl.
*G01N 27/414* (2006.01)

(52) U.S. Cl. .................................. 257/414; 600/353
(58) Field of Classification Search ............... 257/414; 977/720, 721, 723; 361/226; 600/353–364
See application file for complete search history.

(56) References Cited

U.S. PATENT DOCUMENTS 3,860,430 A 1/1975 Walker et al.

(Continued)

FOREIGN PATENT DOCUMENTS

WO WO01/44796 6/2001

(Continued)

OTHER PUBLICATIONS

Deng et al., "Hybrid Composite of Polyaniline Containing Carbon Nanotube", Chinese Chemical Letters, vol. 12, pp. 1037-1040, (2001).*

(Continued)

*Primary Examiner*—Thomas L Dickey
(74) *Attorney, Agent, or Firm*—Weaver Austin Villeneuve & Sampson LLP (57) ABSTRACT

A system for measuring an analyte of interest, particularly carbon dioxide, dissolved in a fluid media of a patient including a nanoelectronic sensor and a measurement instrument in communication with the sensor and configured to receive at least a signal from the sensor indicative of a response of the sensor to at least the analyte of interest.

13 Claims, 7 Drawing Sheets

U.S. PATENT DOCUMENTS

| | | |
|---|---|---|
| 4,795,968 A | 1/1989 | Madou et al. |
| 4,851,195 A | 7/1989 | Matthews et al. |
| 5,246,859 A | 9/1993 | Nelson et al. |
| 5,382,417 A | 1/1995 | Haase |
| 5,618,496 A | 4/1997 | Hasumi et al. |
| 5,759,773 A | 6/1998 | Tyagi et al. |
| 5,958,340 A | 9/1999 | Meyer et al. |
| 6,010,459 A | 1/2000 | Silkoff et al. |
| 6,055,447 A * | 4/2000 | Weil et al. ............... 600/353 |
| 6,090,545 A | 7/2000 | Wohlstadler et al. |
| 6,217,828 B1 | 4/2001 | Bretscher et al. |
| 6,286,226 B1 | 9/2001 | Jin |
| 6,465,132 B1 | 10/2002 | Jin |
| 6,489,394 B1 | 12/2002 | Andros |
| 6,797,325 B2 * | 9/2004 | Wang et al. ............... 427/336 |
| 6,894,359 B2 | 5/2005 | Bradley et al. |
| 2002/0017300 A1 | 2/2002 | Hickle et al. |
| 2002/0092779 A1 | 7/2002 | Essalik et al. |
| 2002/0117659 A1 * | 8/2002 | Lieber et al. ............... 257/14 |
| 2003/0031620 A1 | 2/2003 | Harutyunyan et al. |
| 2003/0041438 A1 | 3/2003 | Wei et al. |
| 2003/0068432 A1 | 4/2003 | Dai et al. |
| 2003/0073919 A1 | 4/2003 | Hampton et al. |
| 2003/0134267 A1 | 7/2003 | Kang et al. |
| 2003/0139003 A1 | 7/2003 | Gole et al. |
| 2003/0171781 A1 * | 9/2003 | Florio et al. ............... 607/17 |
| 2003/0175161 A1 | 9/2003 | Gabriel et al. |
| 2004/0011291 A1 | 1/2004 | Delaunay et al. |
| 2004/0023428 A1 | 2/2004 | Gole et al. |
| 2004/0033525 A1 | 2/2004 | Monforte et al. |
| 2004/0043527 A1 * | 3/2004 | Bradley et al. ............... 438/48 |
| 2004/0067530 A1 | 4/2004 | Gruner et al. |
| 2004/0091285 A1 | 5/2004 | Lewis |
| 2004/0120183 A1 | 6/2004 | Appenzeller et al. |
| 2004/0136866 A1 | 7/2004 | Pontis et al. |
| 2004/0158410 A1 | 8/2004 | Ono et al. |
| 2004/0192072 A1 | 9/2004 | Snow et al. |
| 2004/0219090 A1 | 11/2004 | Dziedzic et al. |
| 2005/0129573 A1 | 6/2005 | Gabriel et al. |
| 2005/0245836 A1 | 11/2005 | Star et al. |
| 2006/0014172 A1 | 1/2006 | Muller et al. |
| 2006/0021881 A1 | 2/2006 | Soundarrajan et al. |
| 2006/0035215 A9 | 2/2006 | Sorge et al. |
| 2006/0040294 A1 | 2/2006 | Prudent et al. |
| 2007/0048180 A1 | 3/2007 | Gabriel et al. |
| 2007/0048181 A1 | 3/2007 | Chang et al. |
| 2008/0021339 A1 | 1/2008 | Gabriel et al. |

FOREIGN PATENT DOCUMENTS

| | | |
|---|---|---|
| WO | WO 2004044586 A1 * | 5/2004 |
| WO | WO2005/026694 | 3/2005 |
| WO | WO2007/114931 | 10/2007 |
| WO | WO2007/136523 | 11/2007 |

OTHER PUBLICATIONS

U.S. Appl. No. 11/390,493, filed Mar. 27, 2006, Ben-Barak et al.

US Office Action dated Jul. 14, 2008 issued in U.S. Appl. No. 11/019,792.

US Office Action dated May 12, 2008 U.S. Appl. No. 11/437,275.

US Office Action dated Apr. 16, 2008 in U.S. Appl. No. 11/488,456.

US Office Action dated Jun. 1, 2005 issued in U.S. Appl. No. 10/940,324.

US Office Action dated Mar. 3, 2006 issued in U.S. Appl. No. 10/940,324.

US Office Action dated Sep. 7, 2006 issued in U.S. Appl. No. 10/940,324.

US Office Action Final dated Feb. 21, 2007 issued in U.S. Appl. No. 10/940,324.

US Examiner Interview Summary dated Feb. 1, 2008 issued in U.S. Appl. No. 10/940,324.

US Office Action dated Aug. 27, 2007 issued in U.S. Appl. No. 10/940,324.

US Office Action Final dated May 27, 2008 issued in U.S. Appl. No. 10/940,324.

US Office Action dated Aug. 12, 2008 issued in U.S. Appl. No. 10/940,324.

International Search Report dated Aug. 7, 2008 issued in WO2007/136523.

International Written Opinion dated Aug. 7, 2008 issued in WO2007-136523.

International Preliminary Examination dated Nov. 27, 2008 issued in WO2007-114931.

International Written Opinion dated Oct. 27, 2008 issued in WO2007-114931.

International Search Report dated Oct. 27, 2008 issued in WO2007-114931.

Preliminary Examination Report and Written Opinion dated Sep. 22, 2005 issued in WO2005/026694.

International Search Report dated Sep. 22, 2005 issued in WO2005/026694.

Deng et al., "Hybrid Composite of Polyaniline Containing Carbon Nanotube," *Chinese Chemical Ltrs*, 12:1037-1040.

Star et al. (2006) "Label-free detection of DNA hybridzation using carbon nanotube network field-effect transistors," *Proc. Nat'l. Acad. Sci. USA.*; vol. 103, No. 4, pp. 921-926; Jan. 24, 2006.

Suri et al. (2002) "Gas and Humidity Sensors Based on Iron Oxide-Polyprrole Nanocomposites," *Sensors and Actuators*, B81:277-282.

* cited by examiner

NANOELECTRONIC MEASUREMENT SYSTEM FOR PHYSIOLOGIC GASES AND IMPROVED NANOSENSOR FOR CARBON DIOXIDE

CROSS-REFERENCE TO RELATED APPLICATIONS

This application is also a continuation-in-part of U.S. patent application Ser. No. 10/656,898 filed Sep. 5, 2003 now abandoned entitled "Polymer Recognition Layers For Nanostructure Sensor Devices" (published as US 2005-0279,987), which in turn claims priority to Provisional Application No. 60/408,547 filed Sep. 5, 2002, which applications are incorporated by reference.

This application is also a continuation-in-part of U.S. patent application Ser. No. 10/773,631 filed Feb. 6, 2004 now abandoned entitled "Analyte Detection In Liquids With Carbon Nanotube Field Effect Transmission Devices", which claims priority to US Provisional Patent Application No. 60/445,654 filed Feb. 6, 2003, which applications are incorporated by reference.

This application is also a continuation-in-part of co-pending U.S. patent application Ser. No. 10/846,072 filed May 14, 2004 entitled "Flexible nanotube transistors" (published as US 2005-0184,641), which claims priority to U.S. Provisional Patent Application No. 60/471,243 filed May 16, 2003, which applications are incorporated by reference.

This application is a continuation-in-part of and claims priority to U.S. patent application Ser. No. 10/940,324 filed Sep. 13, 2004 entitled "Carbon Dioxide Nanoelectronic Sensor" (published as US 2005-0129,573), which in turn claims priority to U.S. Provisional Patent Application No. 60/502,485 filed Sep. 12, 2003, which applications are incorporated by reference.

This application is a continuation-in-part of and claims priority to U.S. patent application Ser. No. 11/019,792 filed Dec. 20, 2004 now U.S. Pat. No. 7,547,931 entitled "Nanoelectronic capnometer adapter" (published as US 2005-0245,836); which in turn claims priority to U.S. Provisional Patent Application No. 60/531,079, filed Dec. 18, 2003, which applications are incorporated by reference.

This application claims priority to U.S. Provisional Patent Applications No. 60/665,153 filed Mar. 25, 2005 entitled "Nanoelectronic Measurement System For Physiologic Gases"; No. 60/668,879 filed Apr. 5, 2005 entitled "Nanoelectronic System For Virus Detection and Identification"; and No. 60/748,834 filed Dec. 9, 2005 entitled "Nanoelectronic Sensors Having Substrates With Pre-Patterned Electrodes, And Environmental Ammonia Control System," which applications are incorporated herein by reference.

FIELD OF THE INVENTION

The present invention relates to sensors, and in particular to nanostructured sensor systems for measurement of medically important physiologic gases during patient care, such as tissue $CO_2$ measurement.

BACKGROUND OF THE INVENTION

As described in U.S. patent application Ser. No. 09/099,293 filed Jun. 18, 1998 (now U.S. Pat. No. 6,055,447) entitled "Patient $CO_2$ Measurement" by M. Weil et al., and other patent applications incorporated by reference herein, methods and apparatus have been developed for sampling of carbon dioxide ($CO_2$) as present in human tissue.

Examples include measurement strategies for determining tissue $CO_2$ by sampling gases diffused across a mucous membrane. In a further example, a system for sublingual measurement of $CO_2$ has been made and marketed as the CapnoProbe by Nellcor Puritan Bennett (Tyco Healthcare/Mallinckrodt). Unfortunately there are challenges involved with this approach (see FDA Press Release P04-82 dated Aug. 27, 2004, which is published on the web as http://www.fda.gov/bbs/topics/news/2004/NEW01108.html).

Each such probe is packaged in a metal canister filled with a saline solution and sealed in a foil envelope labeled as non-sterile. In this instance, the probe and associated saline were reported to contain the bacteria *Burkholderia Cepacia* and other opportunistic pathogens that can cause serious infections, usually in persons who have decreased resistance to infection. This has resulted in the recall of certain devices. The saline storage limitations are related to the detection technology employed. See, for example, U.S. patent application Ser. No. 08/535,878 filed Sep. 28, 1995 by J. Alderete, et al. for "Optical Carbon Dioxide Sensor, and Associated Methods of Manufacture" (now U.S. Pat. No. 5,714,121 assigned to Optical Sensors Incorporated), which is incorporated by reference herein. What is needed is an inexpensive carbon dioxide sensor for reliable, and safe measurement of carbon dioxide that does not require storage in a saline solution to maintain its operational characteristics.

SUMMARY OF THE INVENTION

It should be understood that one aspect of the invention herein may be set forth in one part of the description, figures, formulas, and/or examples herein, while other aspects of the invention may be set forth in other parts of the description, figures, formulas, and/or examples herein. Certain advantageous inventive combinations may be taught in one part of the description, figures, formulas, and/or examples herein, and the detailed description, and the best mode of such combinations and their respective elements may be set forth in other parts of the description, figures, formulas, and/or examples herein. Therefore, the invention is to be understood broadly from this disclosure as read in its entirety, including the patent applications incorporated by reference, and including the claims set forth below. Likewise, any examples or cross-references included in the incorporated patent applications may be instructive with regard to the invention herein, and are therefore incorporated herein by reference.

In exemplary embodiments having aspects of the invention herein, sensors such as the carbon dioxide nanoelectronic sensor described in the co-invented pending US Published Patent Application No. 2005-0129,573 entitled "Carbon Dioxide Nanoelectronic Sensor," which is incorporated herein by reference, are shown herein to provide a practical and economical solution to the certain limitations associated with previously-marketed medical instruments, such as sublingual probes. In contrast to such sensors, a carbon dioxide sensor such as a carbon nanotube-based sensor described in US Published Patent Application No. 2005-0129,573 does not require storage in a saline solution to maintain its operational characteristics. It may be stored in a sealed, sterile dry package (e.g., dry sterile nitrogen), which does not present an environment supportive of growth of bacteria during storage. As described in US Published Patent Application No. 2005-0129,573, and other patent applications incorporated by reference herein, electronic sensors including nanostructure elements have been developed which provide a highly compact, inexpensive (e.g., disposable), low power detector and measurement device for measuring medically important species in human blood, tissue, breath, fluids and the like, for example carbon dioxide, oxygen, hydrogen, nitrous oxide and other gases. In the alternative or in addition the system may include sensors having a sensitivity for biomolecular, biochemical or pharmaceutical species.

A nanoelectronic sensor such as described in US Published Patent Application No. 2005-0129,573 has been previously demonstrated to be effective for measuring $CO_2$ in exhaled breath. See the co-invented pending US Published Patent Application No. 2005-0245,836 entitled "Nanoelectronic Capnometer Adapter," which is incorporated by reference. Likewise, a nanoelectronic sensor such as described in US Published Patent Application No. 2005-0129,573 has been previously demonstrated to be conveniently suited to compact and reliable integration in low-power electronic systems including conventional power supplies, data acquisition, transmission, reception and display components. See the co-invented pending US Published Patent Application No. 2006-0055,392 entitled "Remotely Communicating, Battery-Powered Nanostructure Sensor Devices," which is incorporated by reference.

Furthermore, the described sensors may be conveniently mass-fabricated on tiny substrates, such as a subdivided die of a silicon wafer, lending these sensors to inexpensive manufacture in very small operational packages. The use of silicon wafer technology permits processes and equipment common to the electronics industry to be used. A die comprising the circuitry of one or more sensors may be separated from the wafer. The die may then be packaged, mounted and/or encapsulated by common methods known in the electronics industry so that electrical power and signal conductors of the die communicate with extended electrical leads, either as a discrete sensor component, or as a sub-component of a larger-scale circuit board or electronic device. Alternatively, the sensor circuitry may be formed on the wafer as a functional region of an integrated circuit, and packaged in a manner known for ICs.

Alternatively, sensors such as described in U.S. patent application Ser. No. 10/940,324 may be made on flexible substrate materials, such as polymer films, for example employing devices and method described in the co-invented pending US Published Patent Application No. 2005-0184,641 entitled "Flexible Nanotube Transistors," which is incorporated herein by reference. These devices and methods are suitable for very low cost production, lending them to use in disposable or consumable products.

In certain embodiments, a system having aspects of the invention for measuring an analyte of interest dissolved in a fluid media comprises: an insertion tube having a distal portion and a proximal portion. Note that in alternative embodiments the insertion tube may be variously configured for a particular purpose, such as for access to various body orifices (endo-tracheal tube or sublingual probe), for autonomous body passage (e.g., a gastrointestinal endoscopic capsule), as an implantable therapy device (e.g. a pacemaker), and the like. The system further comprises a nanoelectronic sensor mounted adjacent the distal portion of the tube, the insertion tube configured to place the sensor adjacent at least one lumen or tissue surface of the patient upon insertion of the distal portion into at least one body cavity or lumen of the patient, so as to permit diffusion of the analyte of interest through the surface to the sensor; and a measurement instrument in communication with the sensor and configured to receive at least a signal from the sensor indicative of a response of the sensor to at least the analyte of interest. The sensor includes: a substrate; at least one nanostructured element disposed adjacent the substrate, at least a first conductor in electrical communication with the nanostructured element; at least a second conductor disposed in operative association with the nanoelectronic sensor and configured to electrically influence the at least one nanostructured element upon application of a voltage to the second electrical conductor relative to the first electrical conductor, so as to permit the measurement of at least one electrical property of the at least one nanostructured element; wherein the nanostructured element has a sensitivity to at least one analyte of interest so that the presence of the analyte of interest produces a measurable change in the at least one electrical property of the nanostructured element.

In certain alternative embodiments, the nanostructured element includes one or more carbon nanotubes, such as SWNTs, and may include an interconnecting network of carbon nanotubes. In one alternative, the first and second conductors are configured as a space-apart pair of source-drain electrodes in electrical communication with the nanostructured element; the sensor comprises a gate electrode arranged to capacitively influence the nanostructured element; and the signal includes a transistor characteristic indicative of a response of the sensor to at least the analyte of interest. In another alternative, the second conductors is configured as a capacitive counter electrode arranged to capacitively influence the nanostructured element; and the signal includes at least a capacitance or an impedance indicative of a response of the sensor to at least the analyte of interest.

In certain alternative embodiments, the analyte at least one analyte includes $CO_2$, and the sensor may further include a recognition material, such as an organic polymer, disposed adjacent the nanostructured element, selected to provide a sensitivity to $CO_2$. In certain embodiments the recognition material includes at least one polymer selected from the group consisting essentially of polyvinyl pyridine, polyaniline, polyaminostyrene, PEI, polyvinyl-methylamine, PAMAM, and their cross-linked polymers, which are hydrogels.

In certain alternative embodiments, the insertion tube is configured to place the sensor adjacent at least a surface within the mouth, such as a sublingual surface. In alternative embodiments, the insertion tube is configured to place the sensor adjacent at least a surface within the trachea. In other alternatives, the insertion tube is configured to place the sensor adjacent at least a surface within the digestive tract. Optionally, the system may include a hydrophobic filter element mounted adjacent the insertion tube and arranged to lie between the nanoelectronic sensor and the at least one mucosal surface.

BRIEF DESCRIPTION OF FIGURES

The description of the invention herein includes the following figures:

FIG. 12 illustrates one example of a multi-channel sensor system having aspects of the invention, for use in a treatment area, such as a bedside, an ICU, and the like;

DETAILED DESCRIPTION

Figure 1A:
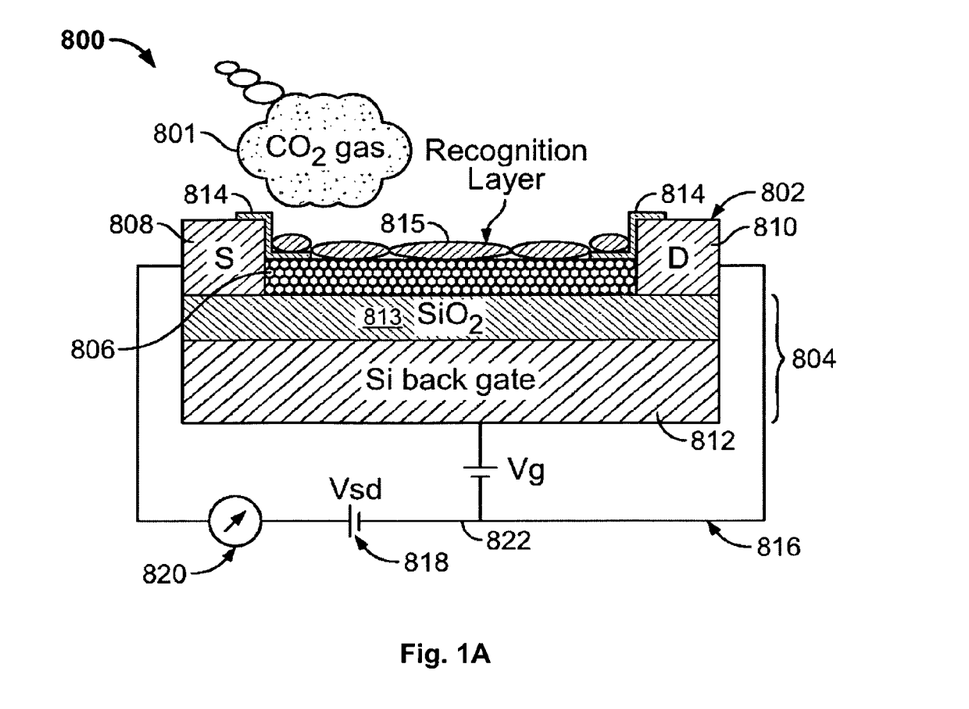
FIG. 1A schematically illustrates an exemplary nanostructure sensor having aspects of the invention, configured as a carbon nanotube FET.

FIG. 1A schematically illustrates an nanostructure sensor 800, such as is described in U.S. patent application Ser. No. 10/940,324, in this example configured as a carbon nanotube field effect transistor or NTFET. FIG. 1A shows an electronic system 800 for detecting carbon dioxide 801, comprising a nanostructure sensing device 802. Device 802 comprises a substrate 804, and a nanostructure 806 disposed over the substrate. The nanostructure may contact the substrate as shown, or in the alternative, may be spaced a distance away from the substrate, with or without a layer of intervening material. In an embodiment of the invention, nanostructure 806 may comprises a carbon nanotube. Any other suitable nanostructure, such as a nanowire, nanofiber, or nanorod, may also be used. In addition, or in the alternative, nanostructure 806 may comprise boron, boron nitride, and carbon boron nitride, silicon, germanium, gallium nitride, zinc oxide, indium phosphide, molybdenum disulphide, silver, or any other suitable material. In an alternative embodiment, nanostructure 806 comprises an interconnected network of smaller nanostructures. For example, nanostructure 806 may comprise a plurality of nanotubes forming a mesh.

Two conductive elements 808, 810 may be disposed over the substrate and electrically connected to nanostructure 806. Elements 808, and 810 may comprise metal electrodes in direct contact with nanostructure 806. In the alternative, a conductive or semi-conducting material (not shown) may be interposed between elements 808, 810 and nanostructure 806. A functionalization material 815 reactive with carbon dioxide is disposed on nanostructure sensing device 802 and in particular, on nanostructure 806. Material 815 may be deposited in a continuous layer, or in a discontinuous layer.

Material 815 may comprise more than one material and/or more than one layer of material, also referred to as "functionalization material," "functionalization layer" or "functionalization." The functionalization layer has two main functions: 1) it selectively recognizes carbon dioxide molecules and 2) upon the binding of $CO_2$ it generates an amplified signal that is transferred to the nanostructure (e.g., carbon nanotube) transducer. Basic inorganic compounds (e.g., sodium carbonate), pH-sensitive polymers, such as polyaniline, poly(ethyleneimine), poly(o-phenylenediamine), poly(3-methylthiophene), and polypyrrole, as well as aromatic compounds (benzylamine, naphthalenemethylamine, anthracene amine, pyrene amine, etc.) can be used to functionalize NTFETs for $CO_2$ sensing. The functionalization layer can be constructed using certain polymeric materials, such as polyethylene glycol, poly(vinyl alcohol) and polysaccharides, including various starches, as well as their components amylose and amylopectin. For example, a suitable reaction layer may be formed from a combination of PEI or similar polymer with a starch polymer. Other suitable materials for the functionalization layer may include, for example, metals, metal oxides, and metal hydroxides. In addition, a metallic functionalization layer may be combined with a polymeric functionalization layer.

Materials in the functionalization layer may be deposited on the NTFET using various different methods, depending on the material to be deposited. For example, inorganic materials, such as sodium carbonate, may be deposited by drop casting from 1 mM solution in light alcohols. The functionalized sensor may then be dried by blowing with nitrogen or other suitable drying agent. Polymeric materials may be deposited by dip coating. A typical procedure may involve soaking of the chip with the carbon nanotube device in 10% polymeric solution in water for 24 hours, rinsing with water several times, and blowing the chip dry with nitrogen. Polymers which are not soluble in aqueous solutions may be spin coated on the chip from their solutions in organic solvents. Values of polymer concentrations and the spin coater's rotation speeds may be optimized for each polymer.

In one exemplary embodiment having aspects of the invention, the functionalization layer 815 includes PAMAM or poly(amidoamine) dendrimer, which has a branched structure suitable for formation of hydrogels. PAMAM is available commercially in a number of types and forms, such as from Dendritic NanoTechnologies, Inc., Dendritech, Inc., and Sigma-Aldrich Co. For example, an ethylenediamine core may have poly(amidoamine) branches with terminal amine groups. See Xu-Ye Wu, Shi-Wen Huang, Jian-Tao Zhang, Ren-Xi Zhuo, "Preparation and Characterization of Novel Physically Cross-linked Hydrogels Composed of Poly(vinyl alcohol) and Amine-Terminated Polyamidoamine Dendrimer," Macromol. Biosci. 2004, 4, 71-75, which is incorporated by reference.

The functionalization layer 815 may be comprised so as to balance hydrophobicity, hydrophilicity and basic properties (e.g., amino polymers), so as to optimize response time and cross-sensitivity to other species in the sample environment, such as relative humidity. The use of thin film coatings or assembled monolayers (SAM) can be employed to improve response time.

Alternative materials for layer 815 may include, for example, those shown in TABLE 3. Such materials may be included in sensors such as are describe herein without departing from the spirit of the invention.

TABLE 3

| Examples of alternative recognition materials | |
|---|---|
| $V_2O_5$ | $WO_3$ |
| Polyacrylic acid | Polyurethane resin |
| Poly(acrylic acid-co-isooctylacrylate) | Polycarbazole |
| poly(ethylene imine), "PEI" | poly(sulfone) |

TABLE 3-continued

Examples of alternative recognition materials

| | |
|---|---|
| poly(4-vinylphenol) | poly(vinyl acetate) |
| poly(alkyl methacrylate) | poly(vinyl alcohol) |
| poly(a-methylstyrene) | poly(vinyl butyral) |
| poly(caprolactone) | Polyacrylamide |
| poly(carbonate bisphenol A) | Polyacrylonitrile |
| poly(dimethylsiloxane) | Polyaniline |
| poly(ethylene glycol) | Polybutadiene |
| poly(ethylene oxide) | Polycarbonate |
| poly(ethylenimine) | Polyethylene |
| poly(methyl vinyl ether-co-maleic anhydride) | Polyoxyethylene |
| poly(N-vinylpyrrolidone) | Polypyrrole |
| poly(propylene) | Polytetrafluoroethylene |
| poly(styrene) | Polythiophene |
| polyvinyl-methyl-amine | Polyvinyl pyridine |
| polyaminostyrene | |
| Chitosan | chitosan HCL |
| Polyallylamine | polyallylamine HCL |
| poly(diallylamine) | poly(diallylamine) HCL |
| poly(entylene-co-vinyl acetate), ~82% ethylene | poly-(m-aminobenzene sulfonic acid), "PABS" |
| poly(styrene-co-allyl alcohol), ~5.7% hydroxyl | poly(vinyl chloride-co-vinyl acetate), ~10%vinyl acetate |
| poly(styrene-co-maleic anhydride), ~50% styrene | poly(vinylidene chloride-co-acrylonitrile), ~80% vinylidene chloride |

Device 802 may further comprise a gate 812. For example, the gate 812 may comprise bulk doped silicon base material of the substrate, electrically isolated by a dielectric or insulating layer 813, e.g. $SiO_2$. Device 802 may further comprise a layer of inhibiting material 814 covering regions adjacent to the connections between the conductive elements 808, 810 and the first nanostructure 806. The inhibiting material may be impermeable to at least one chemical species, such as carbon dioxide. The inhibiting material may comprise a passivation material as known in the art, such as silicon dioxide. Further details concerning the use of inhibiting materials in a NTFET are described in prior U.S. patent application Ser. No. 10/280,265, filed Oct. 26, 2002, which is incorporated by reference herein.

In addition, system 800 may further comprise a second nanostructure sensing device (not shown) like device 802. It may be advantageous to provide the second device with a functionalization layer that incorporates a material different from that incorporated into layer 815. System 800 may further include a nanostructure sensing device circuit 816. Circuit 816 may include one or more electrical supplies 818, a meter 820 in electrical communication with the electrical supply or supplies 818, and electrical connections 822 between the first nanostructure sensing device 802 and both the electrical supply and the meter. System 800 may further comprise a signal control and processing unit (not shown) as known in the art, in communication with the first nanostructure sensing device circuit.

Note that the structure and method illustrated in FIG. 1A are exemplary, and a number of alternative structures and measurement methods are possible without departing from the spirit of the invention. For example, useful sensors having aspects of the invention may omit the application of a gate voltage to the substrate. Alternatively, sensors may provide for measurement of transconductance of the nanostructure subject to a constant or variable source-drain voltage; may provide for measurement of a capacitance of the nanostructure via application of a voltage relative to the gate or other electrode; and/or may include a top gate, side gate, liquid media gate, counter electrode, reference electrode, and the like.

In other alternatives, an electronic device may contain a plurality or array of sensors (or other electronic functional components), preferably fabricated on a single "die" or sheet substrate portion. For example, different sensors may be employed to detect different analytes; may be employed for "pattern recognition" discrimination between chemically similar analytes; may be employed as a graded series of sensors to increase range of concentration sensitivity or precision; and/or as calibration, reference or redundant sensors; and the like. See, for example, U.S. patent application Ser. No. 10/388,701 filed Mar. 14, 2003 entitled "Modification Of Selectivity For Sensing For Nanostructure Device Arrays" (published as US 2003-0175,161) which is incorporated herein by reference.

In addition, the sensor may omit passivation material 814 on the contact regions, or alternatively may include further passivation material or passivation in association with other elements. In other alternatives, the sensor may include conducting or semiconducting elements (not shown in FIG. 1A) to induce additional environmentally-sensitive Schottky barriers at metal/semiconductor junctions with the nanostructures, e.g. a carbon nanotube network may be decorated with metallic particles. See U.S. patent application Ser. No. 10/280,265 filed Oct. 26, 2002 entitled "Sensitivity Control For Nanotube Sensors" (published as US 2004-0043527), and U.S. patent application Ser. No. 10/945,803 filed Sep. 20, 2004 entitled "Multiple Nanoparticles Electrodeposited On Nanostructures," both of which are incorporated herein by reference. In further alternative embodiments having aspects of the invention, the recognition layer 815 may include a plurality of distinct materials or particles; may be disposed upon all or only a portion of the nanostructures; and/or may be disposed on contact conductors, substrate, or as a spaced-apart layer that is electrochemically associated with the nanostructures, or the like.

Figure 1B:
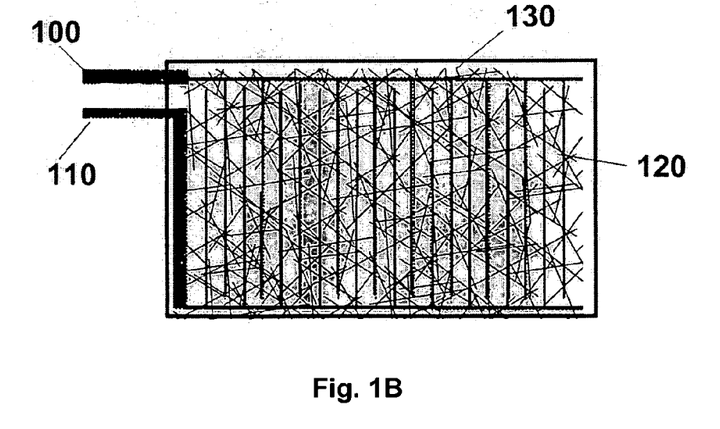
FIG. 1B schematically illustrates an example of a sensor having aspects of the invention employing a random network of carbon nanotubes.

FIG. 1B schematically illustrates an example of a sensor having aspects of the invention employing a random network of carbon nanotubes. A degenerately doped silicon wafer with a silicon oxide film was coated with carbon nanotubes in a random network, as described in U.S. patent application Ser. No. 10/177,929, which is incorporated herein by reference. Titanium contacts 30 nm thick covered with gold contacts 120 nm thick were deposited and patterned by photolithography and lift-off to form opposing contacts 100, 110. Contacts 100, 110 each comprised a plurality of interdigitated portions disposed over a generally rectangular region 130. A network of randomly oriented nanotubes 120 was disposed over the silicon substrate. Nanotubes in the network 120 were in electrical contact with interdigitated portions of contacts 100, 110. After the deposition of the contacts 100, 110, nanotubes outside of the generally rectangular area were removed by oxygen plasma etching, leaving nanotube network 120 remaining. The use of interdigitated sets of metal electrodes 100, 110 with nanotube network 120 interposed generally between the interdigitated contacts results in many nanotubes connected in parallel across the electrodes 100, 110. In one exemplary embodiment, a die was separated from the wafer and mounted in a standard 40-pin chip carrier, with wires connecting the interdigitated wires on the chip to the contacts on the chip carrier. The contact pads and wires on the packages were coated with epoxy resin, which was allowed to cure.

Figure 2:
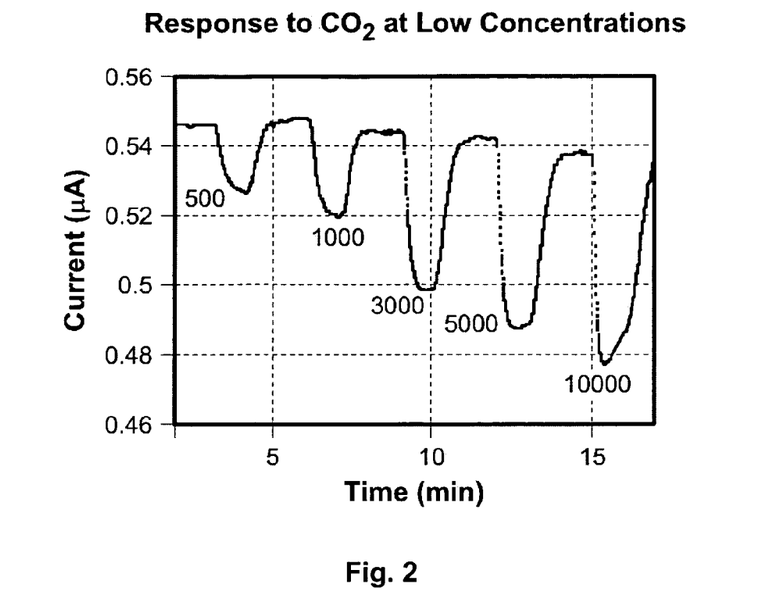
FIG. 2 is a plot of the response of an exemplary nanoelectronic carbon dioxide sensor having aspects of the invention to low concentrations of carbon dioxide.

FIG. 2 is a plot showing the response of an exemplary nano-electronic carbon dioxide sensor having aspects of the invention to a low range of concentrations of carbon dioxide in air. The sensor shows wide dynamic range in the concentration range of 500 to 10,000 ppm. Suitable recognition chemistry and specificity permit the sensor to operate at different relative humidities and shows low cross-sensitivity to other gases (such as oxygen and nitrous oxide).

Figure 3A:
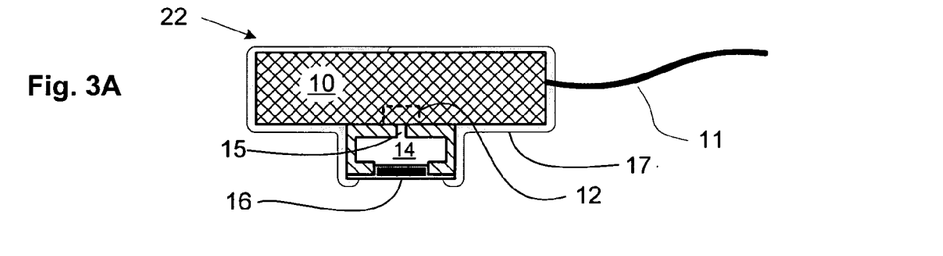
FIGS. 3A and 3B schematically illustrate exemplary embodiments of a sensor device adapted to measure $CO_2$ in the presence of secretions of human mucous membranes, such as within the mouth.
Figure 5:
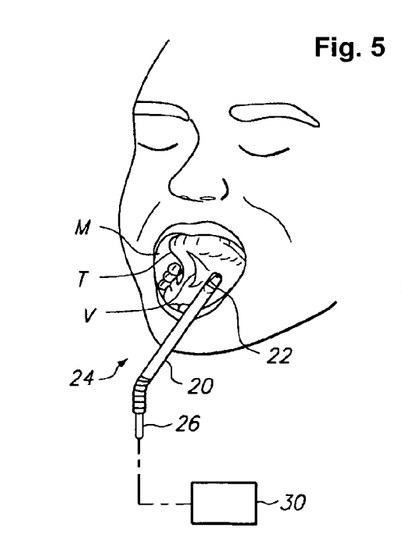
FIGS. 5 and 6 show exemplary methods and sensor systems having aspects of the invention including nanosensors.

FIG. 3A schematically illustrates an exemplary embodiment of a sensor device 22 having aspects of the invention, and adapted to measure $CO_2$ in the presence of secretions of human mucous membranes, such as within the mouth. The sensor device 22 is generally similar to sensors described in the above mentioned U.S. patent application Ser. No. 11/019,792. The exemplary sensor device having aspects of the invention includes a packaged sensor chip 10 having one or more (preferably moisture resistant) signal and/or power conductors 11 extending outward (e.g., to connect via flexible cable 26 to measurement instrument 30, as shown in FIG. 5). Chip package 10 has a sensor opening 12 for communication of analyte media.

In this example, a plenum 14 is mounted adjacent chip package 10, having a pore 15 communication with sensor opening 12. Plenum 14 has a gas-permeable membrane 16 mounted so as to communicate between plenum 14 and the adjacent external environment. The gas-permeable membrane 16 includes a material known in the art and selected so as to permit the diffusion of at least an analyte of interest, in this example carbon dioxide. The analyte of interest is permitted to diffuse through membrane 16, through plenum 14 and pore 15 to sensor package 12. The gas-permeable membrane 16 may include a material known in the art and selected to exclude species other than the analyte of interest, for example, aqueous fluids, such as saliva. For example, the gas-permeable membrane 16 may be a hydrophobic polymer. Additional encapsulation material 17 may be included. Optionally sensor device 22 may include other elements such as filters, absorbents and the like (not shown) to condition analyte media prior to communication with the sensor, e.g. to exclude, repel, deactivate or absorb a particular species (e.g., a contaminant or cross-reacting molecule).

Figure 3B:
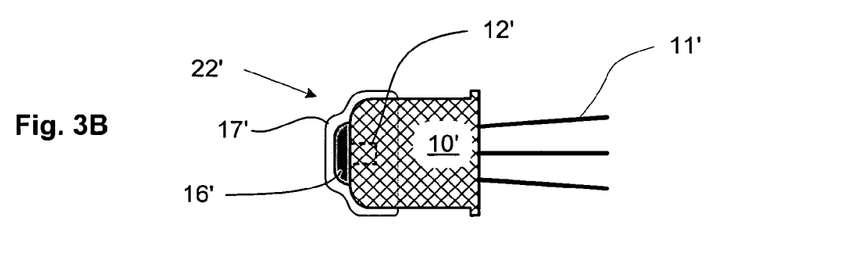

FIG. 3B schematically illustrates an alternative example of a sensor device 22' having aspects of the invention packaged as a discrete sensor component. The components that are similar in form and function to the device of FIG. 3A are denoted by the same number, modified by an '. In this alternative embodiment, the gas-permeable membrane 16' is mounted so as to cover opening 12'.

Figure 4:
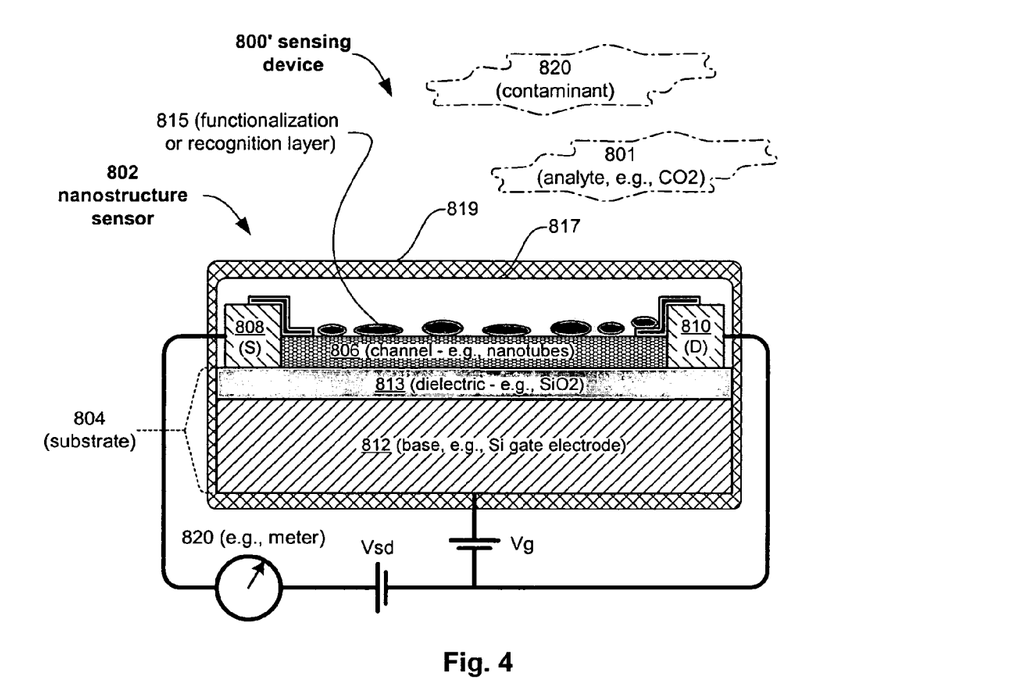
FIG. 4 schematically illustrates an alternative nanostructure sensor, generally similar to the embodiment shown in FIG. 1A, includes optional layers or coatings.

FIG. 4 schematically illustrates an alternative nanostructure FET example of a sensor 800', generally similar to the embodiment shown in FIG. 1A, and bearing like number references for like elements, and FIG. 1A may be referred to for general description. Sensor 800' includes optional layers or coatings 817 and 819.

Layer 817 may be a material, such as a polymer, applied at the "wafer level" or sheet substrate level (e.g. a flexible substrate), whereby an arbitrary plurality of sensor devices are fabricated on a collective substrate (note that a discrete die may include more than one electronic device, such as an array of sensors). Typically such devices or "dies" are subsequently cut, broken or otherwise separated from the bulk wafer or substrate sheet for final packaging and/or integration into an operational electronic system. Note that techniques such as masking, ink jet and/or drop-on-demand printing may be employed to restrict layer 817 to portions of the device if complete coverage is not desired.

Layer or coating 819 may be a material, such as a polymer, applied at the "die" level or separated substrate portion level. This permits encapsulation for the sensor as a unit, for example, a hydrophobic or water-resistant layer to protect substrate, contacts, nanostructures and recognition layer from moisture or another undesired species.

Either or both of layers 817 and 819 may be selected or configured to (a) permit the diffusion or penetration of a particular species (e.g., the analyte of interest) and/or (b) exclude, repel, deactivate or absorb a particular species (e.g., a contaminant or cross-reacting molecule).

Figure 6:
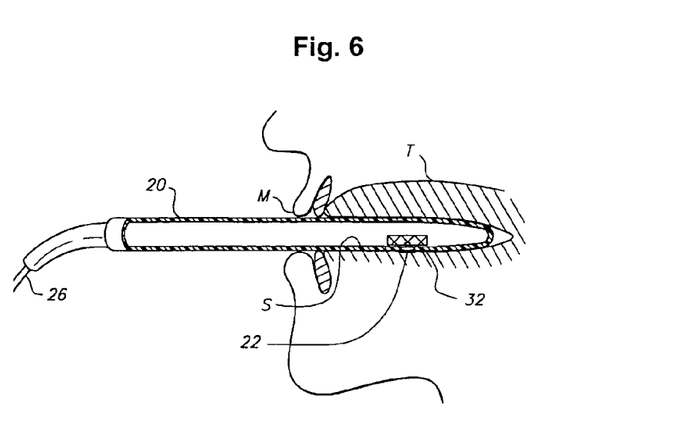

FIGS. 5 and 6 show exemplary methods and sensor systems having aspects of the invention, and which are generally similar in a number of respects to the devices and methods described in the above mentioned U.S. patent application Ser. No. 09/099,293, and also U.S. patent application Ser. No. 09/285,409 filed Apr. 2, 1999 (issued as U.S. Pat. No. 6,258,046), entitled "Method and device for assessing perfusion failure in a patient by measurement of blood flow," both of which are incorporated herein by reference.

FIG. 5 depicts a method of measurement of $CO_2$, in which a tube 20 containing a $CO_2$ sensor 22 at its front end, is inserted into the oral passage and placed under the tongue T of the patient, preferably to one side of the frenulum V. The sensor 22 may be generally similar to the sensor 22, 22' or 802' shown in FIGS. 3-4. After insertion, it would be desirable if the mouth M of the patient is kept closed around the tube, so air does not circulate around the $CO_2$ sensor, which carries away some carbon dioxide. However, with other instruments commonly inserted through the mouth, and with a patient in a critical condition, the patient is usually unable to keep his mouth closed. Also, when the patient breathes through his nose, there is some air flow around the mouth. In this example, the tube 20 and sensor 22 are part of an instrument 24 that includes a flexible cable 26 that extends to a test instrument 30 that typically indicates the partial pressure of $CO_2$ to thereby indicate the degree of perfusion failure. While the tube 20 is preferably substantially rigid, the cable 26 may be flexible. FIG. 6 shows an example of a sensor 22, which lies in contact with the sublingual mucosal surface.

Figure 7:
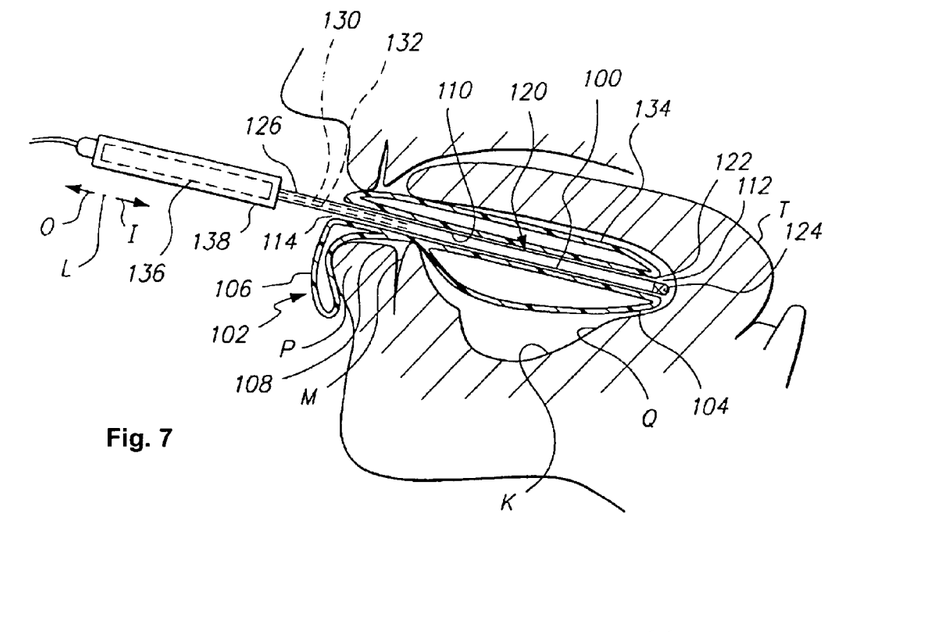
FIG. 7 shows an exemplary method and device having aspects of the invention for taking sublingual partial pressure of carbon dioxide (pCO2) measurements employing nanosensors.

FIG. 7 shows an exemplary method for taking sublingual $pCO_2$ measurements and sensor system having aspects of the invention and which are generally similar in a number of respects to the devices and methods described in the above mentioned U.S. patent application Ser. No. 09/160,224 filed Sep. 24, 1998 (published as U.S. Pat. No. 6,216,024), entitled "Method and device for assessing perfusion failure in a patient." Note that the number references of FIG. 7 do NOT necessarily refer to the same or similar elements as like numbers of FIGS. 5-6.

In this embodiment, sensor assembly instrument 100 is held in position by a sensor holder 102 that lies primarily in a patient's mouth. The sensor holder has a sublingual inner portion 104 that is shaped to fit under the patient's tongue (T), and especially near the location where the tongue merges with the bottom or floor K of the mouth and to lie on the bottom of the mouth. The holder has an outer portion 106 that lies outward of the inner portion and that is accessible from outside the mouth. The particular outer portion 106 lies outside the mouth and has a laterally (L) extending groove or recess 108 with groove walls that rest on the lower denture (M) and lower lip (P) of the patient. The holder 102 forms a holder passage 110 that extends between the inner and outer portions 104, 106 of the holder. The passage has at least inner and outer ports 112, 114 and preferably extends along the entire length of the holder in the inner and outer directions (I), (O).

The sensor assembly 100 has a frame 120 with an inner end 122 that supports a $CO_2$ sensor 124. Sensor 124 of FIG. 7 may be substantially the same as sensor 22, 22' or 802' as shown in FIGS. 3-4. The sensor 124 projects inwardly from the holder and substantially directly contacts the mucosal surface (W) of the patient. The frame has an outer end 126 that lies outside the patient's mouth. Two or more electrical conductors or wires 130, 132 may extend in the frame along the length of the passage between the sensor and an electrical circuit portion 136 mounted in a handle 138, the circuit portion 136 preferably being a preamplifier but possibly being only a connector. Preferably, the sensor is positioned on either side of the frenulum of the tongue. The holder 102 is thus preferably formed with a slot 140 that receives the frenulum, so the sublingual inner portion 104 can lie close to the inner end of the sublingual area and therefore closely around the $CO_2$ sensor. The particular holder shown has two passages 110, 110A that lead to areas on opposite sides of the frenulum. A thermometer can be inserted through the second passage because the level of $CO_2$ is slightly affected by the patient's temperature. A thermometer can be incorporated in the instrument that includes the carbon dioxide sensor.

Figure 8:
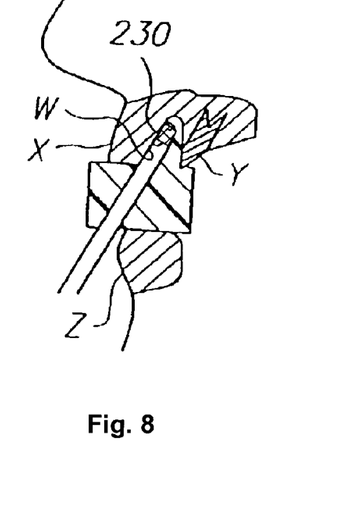
FIGS. 8 and 9 show an exemplary method and sensor system for measuring pCO2 across a mucosal surface.
Figure 9:
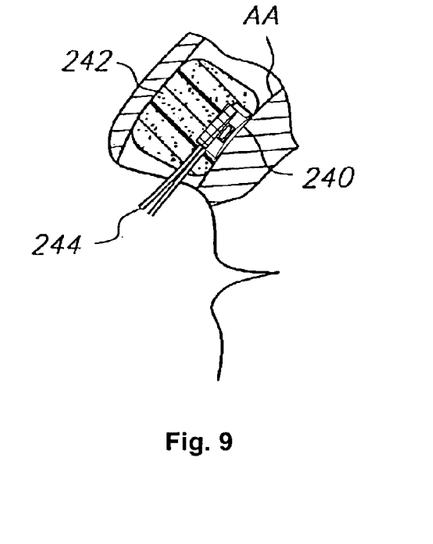

FIGS. 8 and 9 show an exemplary method and sensor system having aspects of the invention, which are generally similar in a number of respects to the devices and methods described in U.S. patent application Ser. No. 09/160,224 filed Sep. 24, 1998 (now U.S. Pat. No. 6,216,024), entitled "Method and device for assessing perfusion failure in a patient," and U.S. patent application Ser. No. 10/357,996 filed Feb. 4, 2003 (published as US 2003-0220551), entitled "Device for assessing perfusion failure in a patient by measurement of blood flow," both of which are incorporated herein by reference.

In an alternative embodiment, the sensor can be placed adjacent any mucosal surface accessible by the mouth or nose and connecting with any region of the GI tract or upper respiratory/digestive tract. For example, in FIG. 8 a sensor 230 can be placed at a gingival mucosal surface W that lies between a lip (X) and the teeth (Y) of the patient. The area at the rear of the upper or lower lips (X), (Z) is a mucosal surface.

In another embodiment, as shown in FIG. 9 the blood-flow sensor 240 lies adjacent a mucosal surface area (AA) in the vestibule of the nasal cavity of a patient. A foam plug 242 serves as a holder that holds the sensor to position it. Only a pair of electrical wires 244 extend from the sensor through the holder. The sensors 230 and 240 of FIGS. 8 and 9 may be substantially the same as sensor 22, 22' or 802' as shown in FIGS. 3-4.

Figure 10:
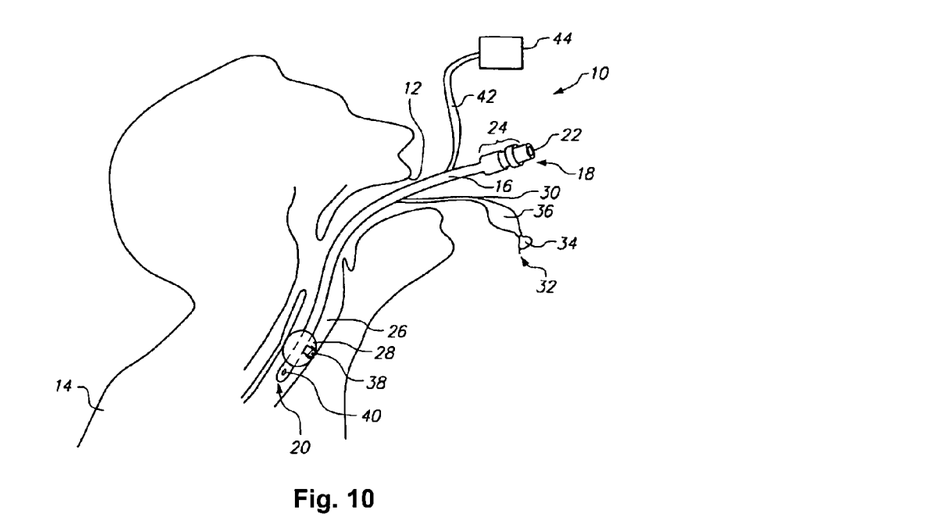
FIG. 10 shows an exemplary method and device having aspects of the invention for taking pCO2 measurements in association with an endotracheal tube.

FIG. 10 shows an exemplary method and sensor system having aspects of the invention, and which are generally similar in a number of respects to the devices and methods described in the above mentioned U.S. patent application Ser. No. 09/252,633 filed Feb. 19, 1999 (now U.S. Pat. No. 6,071, 237), entitled "Device and method for assessing perfusion failure in a patient during endotracheal intubation," which is incorporated herein by reference. Note that the number references of FIG. 10 do NOT necessarily refer to the same or similar elements as like numbers of FIG. 5-6 or 7.

FIG. 10 illustrates a preferred example of a device of the invention, showing an endotracheal tube represented generally as 10 inserted through the mouth 12 of patient 14. The tube can, however, be inserted through the patient's nose or through a tracheotomy. The tube includes a cannula 16 having a proximal end 18 and a distal end 20, wherein the proximal end is provided with a terminal orifice 22 and a connector 24 for connection to a breathable air supply for introduction of gases to the patient's lungs. The distal end 20 of the cannula is shown placed within trachea 26 of the patient. The endotracheal tube is provided with a sealing means for maintaining an air seal between the cannula and the trachea. Preferably, the tube is a conventional "cuffed" tube having as the sealing means an inflatable cuff shown at 28 in an inflated state as it would be during a surgical procedure. Both the cuff and the cannula are preferably generally constructed of radio-opaque bio-compatible material, such as polyvinyl chloride, but as will be appreciated by those skilled in the art, other suitable materials may be substituted therefor. The cuff 28 is inflated by introduction of air into cuff inflation line 30 by attachment of a syringe or the like to the open terminus 32 of the cuff inflation line. The flow of air that is introduced into open terminus 32 of the cuff inflation line 30 is controlled by valve 34, with inflation of pilot balloon 36 indicating inflation of the cuff.

A $pCO_2$ sensor 38 is shown attached to the exterior of cuff 28 and lying against the inside wall of the patient's trachea, but as will be appreciated by those skilled in the art and as described elsewhere herein, the $pCO_2$ sensor is not necessarily positioned on cuff 28. The sensor 38 of FIG. 10 may be generally similar to the exemplary sensors 22, 22' or 802' shown in FIGS. 3-4. The $pCO_2$ sensor may be incorporated within or attached to endotracheal tube 10 in such a way as to be positioned adjacent to and preferably contact the inner wall of the patient's trachea 26. The $pCO_2$ sensor may be operably connected through a flexible cable or catheter 42 to a test instrument 44 including an indicator or display that typically indicates the partial pressure of $CO_2$ in millimeters of mercury (mmHg), which provides an indicia of a degree of perfusion failure.

To place the device so that $pCO_2$ measurements can be made within the patient's trachea, the endotracheal tube 10 may be inserted into the mouth or nose of the patient, or through a tracheotomy, extended through the pharynx and larynx, and into the trachea 26. The tube 10 is preferably sufficiently long so that the proximal end 18 of the cannula and the terminus 32 of the cuff inflation line 30 extend beyond the patient's mouth while the distal end 20 of the cannula is in the patient's trachea 26. After insertion of the endotracheal tube 10, the proximal end 18 of the cannula is attached through terminal orifice 22 and connector 24 to a supply of breathable air (not shown). A positive pressure of air in the lungs is maintained by pumping air from the breathable air supply by introduction of air into terminal orifice 22, through cannula 16 and into the patient's trachea 26 through aperture 40 present at the distal end of the cannula. Prior to introducing air in this way, cuff 28 is inflated by introducing air into the cuff inflation line 30 by a syringe or the like. When the cuff is inflated, the cuff 28 conforms to the natural shape of the trachea while providing a seal with the trachea wall. Inflation of the cuff also forces $pCO_2$ sensor against the trachea wall.

Figure 11A:
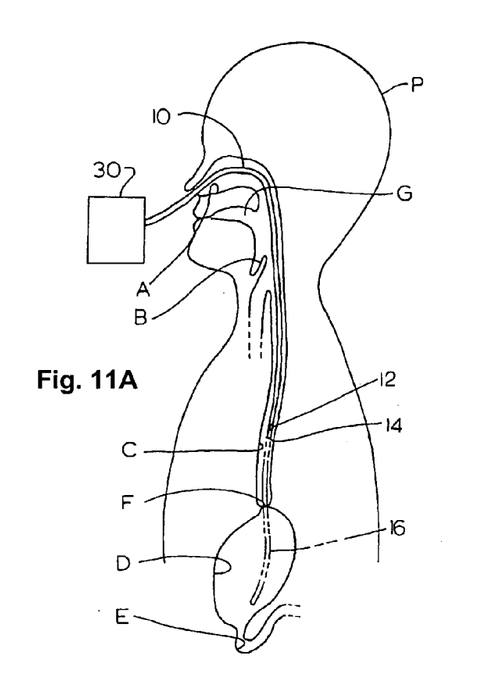
FIGS. 11A, 11B and 11C show an exemplary method and device for measuring pCO2 in a digestive tract.
Figure 11B:
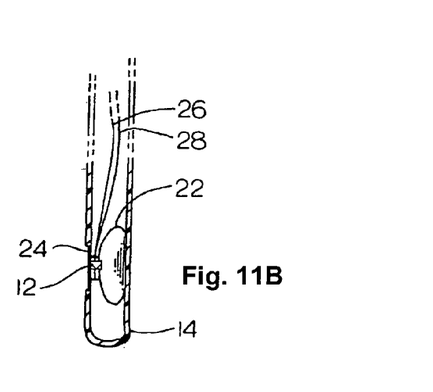
Figure 11C:
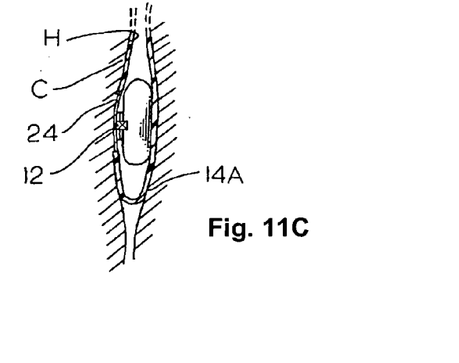

FIGS. 11A, 11B and 11C show an exemplary method and sensor system having aspects of the invention, which are generally similar in a number of respects to the devices and methods described in the above mentioned U.S. patent application Ser. No. 08/498,932 filed Jul. 6, 1995 (now U.S. Pat. No. 5,579,763), entitled "Measurement of systemic perfusion," which is incorporated herein by reference. Note that the number references of FIGS. 11A-C do NOT necessarily refer to the same or similar elements as like numbers of FIG. 5-6, 7 or 10.

FIG. 11A illustrates the nasal passage (A) of a person and part of the digestive system of a person (P), including the epiglottis (B), the esophagus (C), the stomach (D), and a portion of the intestines (E). Blood vessels (not shown) which carry blood to the walls of all of these portions of the digestive tract, typically experience severely reduced perfusion in the event of perfusion failure. That is, when there is a reduced flow of blood from the heart, the body directs a higher portion to organs such as the brain which will not survive long without a continuous supply of blood, while restricting the flow to the stomach and intestines whose survival is not threatened by a temporary large reduction in flow.

As a result, it is common for physicians to assess perfusion failure by taking measurements in the stomach and intestine which indicate the level of blood flow thereat. A useful measurement is the partial pressure of carbon dioxide ($pCO_2$). A large partial pressure of $CO_2$ indicates that there is a low blood flow to carry away carbon dioxide resulting from metabolism. It is noted that an increase in $CO_2$ results in a decrease in pH, and it is also common to measure the pH in the stomach and intestines in perfusion failure. Measurements of $CO_2$ in the stomach or intestines may have deleterious side effects. One side effect is the trauma or harm to the patient caused by insertion of a catheter with a $CO_2$ sensor through the nasal passages, esophagus, esophageal sphincter, into the stomach. Another side effect which affects accuracy of the measurement, is that digestion fluids remaining in the stomach or intestines, can produce $CO_2$. This is especially likely for foods, such as carbohydrates, that are being decomposed and that produce bicarbonate that reacts with stomach acid.

As shown in FIGS. 11A-C, in a preferred embodiment a measurement of perfusion failure is obtained by measuring the $pCO_2$ in the esophagus of the patient, instead of only in the stomach and/or intestine of the patient. The method includes inserting a catheter 10 with a $CO_2$ sensor 12 at the end, through the nasal passage (A) (it is sometimes acceptable to insert the catheter through the oral passage G), past the epiglottis (B), and into the esophagus (C), with the end of the catheter 14 and the sensor 12 which lies nearby, both lying within the esophagus. That is, the sensor 12 lies on a side of the esophagal sphincter (F) which is opposite to the stomach (D). The sensor 12 of FIG. 10 may be generally similar to the exemplary sensors 22, 22' or 802' shown in FIGS. 3-4.

One advantage of this procedure is that there is reduced invasion of the patient because the catheter does not have to pass through the esophageal sphincter (F) or lie in the stomach (D). Another advantage is that $CO_2$ generated in the stomach (D) by digestion fluids does not affect the measurement of $CO_2$ since the esophageal sphincter (F) blocks such gas. It is noted that sometimes the catheter must extend to the stomach as to evacuate it, as indicated at 16. In that case, the sensor 12 will lie along the catheter and be spaced from the distal end of the catheter.

FIG. 11B indicates the construction of the end potion 14 of a catheter, showing the sensor 12 held on a mount 22 within the catheter, and separated by a $CO_2$-preamble membrane 24 from the outside of the catheter. It is possible to mount the sensor on the outside of the catheter to directly engage the esophagus walls. A pair of electrical wires or signal conductors 28, 28 pass signals to a control 30 which indicates the partial pressure of $CO_2$.

FIG. 11C shows the end portion of the catheter at 14A, after it has been inserted into the esophagus and retained thereat. The walls (G) of the esophagus (C) contract around the catheter, resulting in the transistor sensor 12 and the membrane 24 being pressed firmly against the walls of the esophagus, which provides intimate contact for rapid and accurate measurement of $pCO_2$. Because of the natural tendency of the esophagus to contract around the catheter, it is generally not necessary to inflate a balloon at the end of the catheter in order to assure firm engagement of a sensor with the walls of the esophagus. A considerable advantage results from avoiding inflation of a balloon to produce firm engagement of the sensor (which may be a balloon containing a quantity of saline solution) with the esophagus walls. If the balloon inflation pressure is too great, it can constrict blood vessels at the esophagus walls, which can affect $CO_2$ readings.

Figure 12:
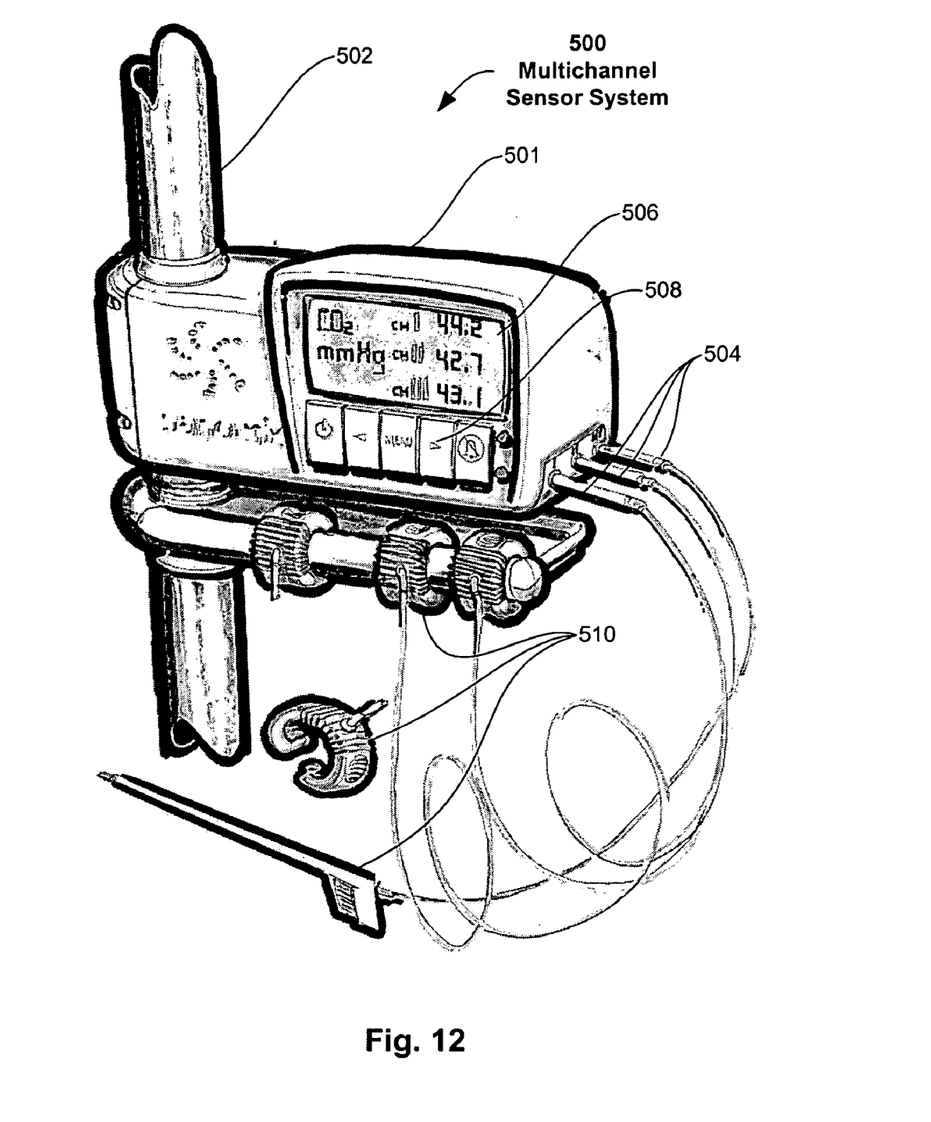

FIG. 12 illustrates one example of a multi-channel sensor system 500 having aspects of the invention, comprising a console 501 mounted to a support 502 for convenient placement in a treatment area, such as a bedside, an ICU, and the like. Preferably, a plurality of cable plugs 504 are disposed on the console 501 to receive a corresponding plurality of cables from measurement instruments 510. The instruments may be anyone of a variety of devices for measurement of $CO_2$ or other analytes of interest, such as any of the devices described in FIGS. 5-11 above, and the like. The devices 510 are shown arranged for convenience of illustration. Typically, the devices 510 will be packaged as pre-sterilized sealed units, which may be disposable or have disposable portions, the sterile device 510 being preferably unsealed and connected to the console 501 immediately prior to measurement, to avoid risk of accidental cross-contamination. A multichannel display 506 and user interface 508 are also disposed on the console 501.

Figure 13:
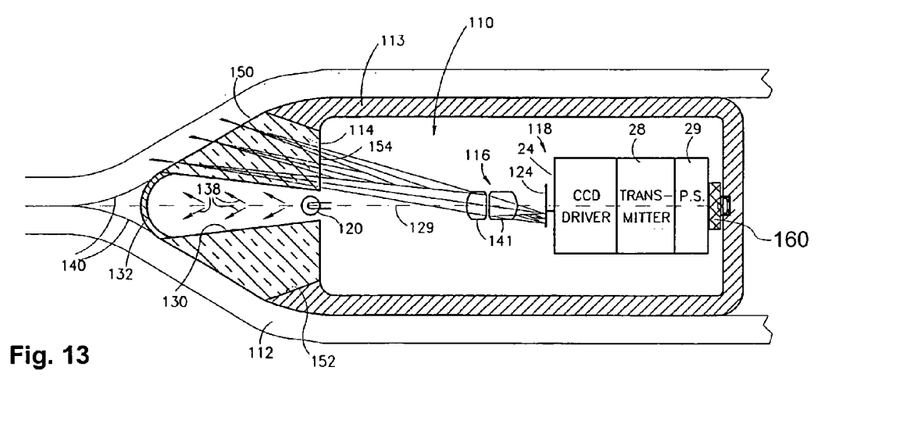
FIG. 13 illustrates an embodiment of a swallowable autonomous gastrointestinal video endoscope capsule having a sensor having aspects of the invention.

FIG. 13 illustrates an embodiment of a swallowable autonomous gastrointestinal video endoscope capsule, similar in general aspects to transmitting capsules described in U.S. Pat. No. 5,604,531 entitled "In vivo video camera system," and U.S. Pat. No. 6,584,348 entitled "Method for measurement of electrical characteristics of tissue," which are incorporated herein by reference. Capsule 110 is shown within a digestive tract lumen 112 having inner walls 140, and comprises a housing 113, a transmitter 28, power source 29 and an optical system aligned to optical axis 129 including axicon optical element 114 (having an outer surface 150, sides 152 and an inner surface 154), relay lens unit 116 (lenses 141, light source 120 (within borehole 130 covered by a rounded cap 132), and image detector 118. The image detector 118 comprises a detector 124 (e.g., a CCD) and driver 126.

Capsule 110 includes one or more sensors 160 having aspects of the invention, for example for measuring $CO_2$ concentration within the intestinal lumen 112. Transmitter 28 is configured to transmit either or both of video and sensor data to a receiving a corresponding reception system (not shown).

Figure 14:
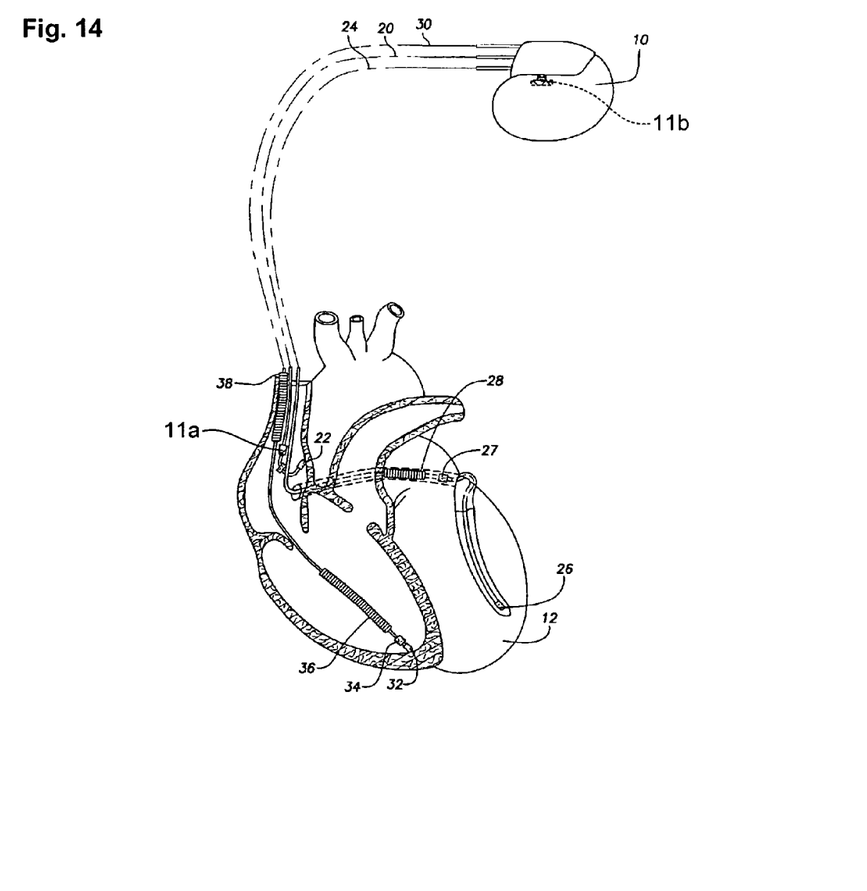
FIG. 14 illustrates one example of an implantable cardiac stimulation device 10 suitable for treating cardiac arrhythmias and having an implantable sensor having aspects of the invention.

FIG. 14 illustrates one example of an implantable cardiac stimulation device 10 suitable for treating both fast and slow arrhythmias with stimulation therapy, including cardioversion, defibrillation, and pacing stimulation, similar in general aspects to a device described in U.S. Pat. No. 7,006,868 entitled "Method and apparatus for using a rest mode indicator to automatically adjust control parameters of an implantable cardiac stimulation device," which is incorporated herein by reference. In the example shown, the device 10 is in electrical communication with a patient's heart 12 via stimulation leads 20, 24 and 30. The right atrial lead 20 has a atrial tip electrode 22 implanted in the patient's right atrial appendage. The "coronary sinus" lead 24 receives atrial and ventricular cardiac signals and delivers pacing and defibrillation shocking therapy via left ventricular tip electrode 26, left atrial ring electrode 27, and left atrial coil electrode 28. The right ventricular lead 30 is capable of receiving cardiac signals, and delivering stimulation in the form of pacing and shock therapy to the right ventricle via right ventricular tip electrode 32, right ventricular ring electrode 34, right ventricular coil electrode 36, and SVC coil electrode 38.

In existing implantable pacing devices, the stimulation therapy may be adjusted by internal electronic logic controls so that the heart rate approximates the demands created by variable patient activity level. Typically on-board accelerometers are used for this purpose, using a variety of algorithms to estimate patient cardiac demand. See, for example, the above referenced U.S. Pat. No. 7,006,868, and also U.S. Pat. No. 6,937,900 entitled "AC/DC multi-axis accelerometer for determining patient activity and body position," which is incorporated herein by reference.

Device 10 includes one or more implantable sensors (e.g., 11a and/or 11b as shown) having aspects of the invention, for example for measuring arterial, venous and/or interstitial $CO_2$ concentration. Sensor 11a is configured to be mounted compactly adjacent a selected electrode of the stimulation leads, e.g., adjacent electrode 22, communicating to device 10 via conductors within lead 20. Sensor 11b is mounted within device 10 so as to communicate with the adjacent tissue. In contrast to or in addition to accelerometers as sensors of activity level, data from the sensors 11a,b may be used for, among other things, determining an activity level, oxygen demand and/or perfusion status of a patient. Cardiac stimulation may then be adjusted in response to such sensor data using conventional electronic controls.

Having thus described preferred embodiments of the methods and devices having aspects of the invention, it should be apparent to those skilled in the art that certain advantages of the within system have been achieved. It should also be appreciated that various modifications, adaptations, and alternative embodiments thereof may be made within the scope and spirit of the present invention. For example, devices and methods generally similar to those described above may be employed for measurement of gases and other analytes in different environments and industrial fields, such as the measurement of $CO_2$ concentration in soils, aqueous environments and the like.

We claim:

1. A system for measuring an analyte of interest dissolved in a fluid media, comprising:
    (a) an insertion tube having a distal portion and a proximal portion, wherein the insertion tube comprises an implantable cardiac stimulation device housing the sensor in communication with a tissue surface;
    (b) a nanoelectronic sensor mounted adjacent the distal portion of the tube, the insertion tube configured to place the sensor adjacent at least one mucosal surface of the patient upon insertion of the distal portion into at least one body cavity or lumen of the patient, so as to permit diffusion of the analyte of interest through the mucosal surface to the sensor; the sensor including:
        (i) a substrate;
        (ii) at least one nanostructured element disposed adjacent the substrate, wherein the nanostructured element has a sensitivity to at least one analyte of interest so that the presence of the analyte of interest produces a measurable change in the at least one electrical property of the nanostructured element;
        (iii) at least a first conductor in electrical communication with the nanostructured element;
        (iv) at least a second conductor disposed in operative association with the nanoelectronic sensor and configured to electrically influence the at least one nanostructured element upon application of a voltage to the second electrical conductor relative to the first electrical conductor, so as to permit the measurement of at least one electrical property of the at least one nanostructured element;
        (v) a recognition material disposed adjacent the nanostructured element, wherein the recognition material includes at least one polymer, selected from the group consisting essentially of polyvinyl pyridine, polyaniline, polyaminostyrene, PE1, polyvinyl-methylamine, PAMAM, and hydrogels thereof;
    (c) a hydrophobic filter element mounted adjacent the insertion tube and arranged to lie between the nanoelectronic sensor and the at least one mucosal surface; and
    (d) a measurement instrument in communication with the sensor and configured to receive at least a signal from the sensor indicative of a response of the sensor to at least the analyte of interest.

2. The system of claim 1, wherein the analyte at least one analyte includes CO2.

3. The system of claim 1, wherein the nanostructured element includes one or more carbon nanotubes.

4. The system of claim 3, wherein the nanostructured element includes an interconnecting network of carbon nanotubes.

5. The system of claim 1, wherein the first and second conductors are configured as a spaced-apart pair of source-drain electrodes in electrical communication with the nanostructured element, and further comprising a gate electrode arranged to capacitively influence the nanostructured element; and wherein the signal includes a transistor characteristic indicative of a response of the sensor to at least the analyte of interest.

6. The system of claim 1, wherein the second conductors are configured as a capacitive counter electrode arranged to capacitively influence the nanostructured element; and wherein the signal includes at least one of a capacitance and an impedance indicative of a response of the sensor to at least the analyte of interest.

7. The system of claim 1, wherein the insertion tube is configured to place the sensor adjacent at least a surface within the mouth.

8. The system of claim 7, wherein the surface within the mouth includes a sublingual surface.

9. The system of claim 1, wherein the insertion tube is configured to place the sensor adjacent at least a surface within the trachea.

10. The system of claim 1, wherein the insertion tube is configured to place the sensor adjacent at least a surface within the digestive tract.

11. The system of claim 1, wherein the insertion tube comprises a swallowable gastrointestinal endoscopic capsule housing the sensor in communication with the digestive tract.

12. The system of claim 1, wherein the insertion tube comprises an implantable cardiac stimulation device housing the sensor in communication with a tissue surface.

13. A system for measuring an analyte of interest dissolved in a fluid media, comprising:
    (a) an insertion tube having a distal portion and a proximal portion, wherein the insertion tube comprises an electrical lead associated with an implantable cardiac stimulation device, the lead mounting the sensor in communication with a vascular lumen;
    (b) a nanoelectronic sensor mounted adjacent the distal portion of the tube, the insertion tube configured to place the sensor adjacent at least one mucosal surface of the patient upon insertion of the distal portion into at least one body cavity or lumen of the patient, so as to permit diffusion of the analyte of interest through the mucosal surface to the sensor; the sensor including:
        (i) a substrate;
        (ii) at least one nanostructured element disposed adjacent the substrate, wherein the nanostructured element has a sensitivity to at least one analyte of interest so that the presence of the analyte of interest produces a measurable change in the at least one electrical property of the nanostructured element;

(iii) at least a first conductor in electrical communication with the nanostructured element;

(iv) at least a second conductor disposed in operative association with the nanoelectronic sensor and configured to electrically influence the at least one nanostructured element upon application of a voltage to the second electrical conductor relative to the first electrical conductor, so as to permit the measurement of at least one electrical property of the at least one nanostructured element;

(v) a recognition material disposed adjacent the nanostructured element, wherein the recognition material includes at least one polymer, selected from the group consisting essentially of polyvinyl pyridine, polyaniline, polyaminostyrene, PE1, polyvinyl-methylamine, PAMAM, and hydrogels thereof;

(c) a hydrophobic filter element mounted adjacent the insertion tube and arranged to lie between the nanoelectronic sensor and the at least one mucosal surface; and (d) a measurement instrument in communication with the sensor and configured to receive at least a signal from the sensor indicative of a response of the sensor to at least the analyte of interest.

* * * * *